(12) United States Patent
Grasruck et al.

(10) Patent No.: US 7,840,043 B2
(45) Date of Patent: Nov. 23, 2010

(54) METHOD FOR AN X-RAY MACHINE

(75) Inventors: Michael Grasruck, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1143 days.

(21) Appl. No.: 11/499,662

(22) Filed: Aug. 7, 2006

(65) Prior Publication Data

US 2007/0030944 A1   Feb. 8, 2007

(30) Foreign Application Priority Data

Aug. 8, 2005 (DE) .................. 10 2005 037 367

(51) Int. Cl.
  *G06K 9/00* (2006.01)
(52) U.S. Cl. ..................................... 382/128
(58) Field of Classification Search .............. 382/128
  See application file for complete search history.

(56) References Cited

U.S. PATENT DOCUMENTS

| | | | | |
|---|---|---|---|---|
| 6,067,371 A * | 5/2000 | Gouge et al. | ................ | 382/128 |
| 6,343,111 B1 | 1/2002 | Avinash et al. | | |
| 6,345,113 B1 * | 2/2002 | Crawford et al. | ............ | 382/131 |
| 6,898,263 B2 * | 5/2005 | Avinash et al. | ................ | 378/4 |
| 7,020,316 B2 * | 3/2006 | Wei et al. | ..................... | 382/131 |
| 2003/0095630 A1 | 5/2003 | Avinash et al. | | |
| 2003/0152259 A1 * | 8/2003 | Belykh et al. | ............... | 382/132 |
| 2004/0252873 A1 | 12/2004 | Avinash et al. | | |
| 2005/0123093 A1 | 6/2005 | Lawaczeck et al. | | |
| 2005/0185829 A1 * | 8/2005 | Heismann | ................... | 382/128 |

FOREIGN PATENT DOCUMENTS

| | | |
|---|---|---|
| DE | 103 53 882 A1 | 6/2004 |
| DE | 103 47 961 A1 | 6/2005 |

OTHER PUBLICATIONS

FujiFilm Co., H.Chikugo et al.: "Upright Image Reader that Supports Energy Subtraction Processing Software", Fuji Computed Radiography—Technical Review No. 12.

* cited by examiner

*Primary Examiner*—Bhavesh M Mehta
*Assistant Examiner*—Hadi Akhavannik
(74) *Attorney, Agent, or Firm*—Harness, Dickey & Pierce, P.L.C.

(57) ABSTRACT

A method is for determining a parameter in an image area as a measure of a homogeneity of a substance in an object, and to a method for segmenting a substance in an image that uses the parameter as an additional segmentation criterion. In the method, at least two X-ray images are acquired in relation to different energies $E_1$, $E_2$ of an X-radiation, and the parameter is determined from the statistical distribution of attenuation values $Di(E_1)$, $Di(E_2)$ where $i=1, \ldots, N$ in the image area such that faulty classifications can be avoided in a simple way during the segmentation.

19 Claims, 4 Drawing Sheets

METHOD FOR AN X-RAY MACHINE

PRIORITY STATEMENT

The present application hereby claims priority under 35 U.S.C. §119 on German patent application number DE 10 2005 037 367.4 filed Aug. 8, 2005, the entire contents of which is hereby incorporated herein by reference.

FIELD

The invention generally relates to a method for an X-ray machine for determining a parameter, and/or to a method for an X-ray machine for segmenting a substance in an image acquired by the X-ray machine.

BACKGROUND

Different substances exhibit different absorption properties with reference to X-radiation as a function of the energy of the X-radiation. On the basis of the different absorption properties, an image in which substantially only a single substance still remains visible can be calculated by a weighted subtraction of a high energy X-ray image from a low energy X-ray image.

Such a method is known, for example, from FujiFilm Co, Technical review no. 12, "Upright image reader that supports energy subtraction processing software". The low energy X-ray image and the high energy X-ray image are acquired by means of an energy-selective detector and calculated with one another to form a result image in which essentially either bone tissue or soft tissue is present. The calculation of the result image is performed at the level of individual pixels, the attenuation values of respectively corresponding pixels of the two X-ray images being subtracted from one another while taking account of substance-specific weights.

The substance-specific weighting takes account of the fact that in the case of two different energies of the X-radiation a defined pair of attenuation values is produced for the substance under ideal boundary conditions in relation to each pixel of the result image. If the two attenuation values relating to the different energies of the X-radiation are regarded as a pair of measured values of a two-dimensional feature space, the pairs of measured values of a substance are thus respectively imaged at the same point in the feature space.

The calculation, referred to individual pixels, of a result image, for example a segmented image, leads, however, in many situations to a defective result. A substantial reason is to be seen in that the segmentation criterion with the aid of which the presence of the substance is decided is based on the assumption that the two attenuation values are produced on the basis of a defined composition of the substance. However, in many situations the actually existing composition of the substance deviates substantially from the ideally assumed composition. Moreover, the attenuation values are falsified by measurement noise. Pairs of measured values of the substance are then not imaged onto one point in the feature space.

Under real examination conditions, different substances can be imaged onto zones in the feature space that exhibits an intersection set. Thus, for example, pairs of measured values of the two different substances of bone and iodine solution that are produced in conjunction with a set voltage of 80 and 140 kV are imaged onto zones with an intersection set in the range between approximately 100 HU (Hounsfield Units) and 200 HU. A unique assignment of these pairs of measured values to a substance is not possible in principle on the basis of an evaluation only of pixels corresponding to the two attenuation values.

SUMMARY

A method, in at least one embodiment, is specified for an X-ray machine with the aid of which a segmentation of a substance on the basis of at least two X-ray images acquired in relation to different energies of an X-radiation is improved.

The inventors, in at least one embodiment, have realized that a segmentation of a substance in an X-ray image acquired by the X-ray machine can be improved when the attenuation values acquired in relation to different energies of an X-radiation are evaluated not only for a single pixel, but for pixels of a local neighborhood. The evaluation in an image area offers the advantage that it is possible to calculate, from a statistical distribution of the pairs of measured values formed from the attenuation values, a parameter that represents a measure of the homogeneity of the substance. The parameter thus determined represents an additional segmentation criterion with the aid of which the segmentation of the substance in an image can be improved.

Pairs of measured values that, for example, fall into the intersection set of point clouds from two different substances, and can therefore not be assigned uniquely on the basis of a purely pixel-based evaluation of the attenuation values, can be classified in an improved way on the basis of the determined parameters for the homogeneity of the substance and an appropriate prior knowledge of the distribution of the substance in the object.

At least one embodiment of the present invention correspondingly proposes a method for the X-ray machine for determining the parameter in an image area as a measure of the homogeneity of the substance in the object, a) in the case of which two X-ray images that have attenuation values that represent an attenuation of the X-radiation passing through the object are acquired for at least two different energies of an X-radiation, b) in the case of which in the image area measured value pairs are formed for corresponding pixels from the attenuation values of the X-ray image acquired in relation to the first energy of the X-radiation, and from the attenuation values of the X-ray image acquired in relation to the second energy of the X-radiation, and c) in the case of which the parameter is determined as a measure of the homogeneity of the substance of the object by evaluating the statistical distribution of the measured value pairs in the image area.

The evaluation of the statistical distribution advantageously comprises a principle axis transformation for calculating two principle axes of the distribution so as to ensure a determination of the parameters that is independent of the measurement situation. The calculation of the parameters is invariant with the principle axis transformation, particularly with reference to image scales of the substance, a measurement noise and the location of the considered pixel, and so there is no need for additional normalizations of the parameters as a function of the measurement situation.

The parameter is preferably calculated from a quotient of the two principle axes, the quotient being formed with the smaller of the two principle axes in the numerator and the larger in the denominator. The preferred direction of the spatial extent of the distribution is acquired in a simple way by the quotients of the two principle axes.

The quality level with which the homogeneity of the substance can be determined is a function of the number of the pixels in the local neighborhood that are used to calculate the parameter. The greater the number of pixels considered in the calculation, the less is the influence of measurement noise on the determination of the parameter. The image area that is used for the calculation therefore advantageously extends at least over 5 pixels in each image dimension.

The acquired X-ray images are advantageously volume images of the object such that a voxel of a three-dimensional image corresponds to each pixel. However, it is likewise conceivable that the X-ray images are tomograms of the object, a pixel of a two-dimensional volume image corresponding in this case to each pixel.

The X-ray images acquired in relation to different energies of an X-radiation can be recorded in a simple way with aid of a conventional X-ray machine having an X-ray source in the form of an X-ray tube, the first X-ray image being acquired with an X-ray voltage set at 80 kV, and the second X-ray image being acquired with an X-ray voltage set at 140 kV. The difference between the energies of the X-radiation on the basis of the different X-ray voltage is so large in this case during acquisition of the two X-ray images that the substances can be segmented particularly well on the basis of their different absorption properties by evaluating the attenuation values.

The parameter is advantageously independent of an offset of the attenuation values when, before method step b) in which the statistical distribution of the pairs of measured values is determined, the attenuation values of the two X-ray images are respectively normalized in the image area by subtracting from the respective attenuation value a mean attenuation value calculated in the image area of the respective X-ray image.

Interference in the calculation of the parameter by pairs of measured values that do not originate in the image area from the substance, are advantageously largely avoided by virtue of the fact that those attenuation values that do not belong to the substance are identified and removed in a preprocessing stage before method step b).

The identification of attenuation values not belonging to the substance can advantageously be performed by calculating the attenuation values of corresponding pixels with one another and comparing them with a threshold value.

The substance for which the parameter is calculated can advantageously be bone. It could likewise also be conceivable to select any other desire substance to calculate the parameter: preferably the iodine present in the contrast medium in the case of a contrast medium examination, for example.

A method, in at least one embodiment, is for an X-ray machine for segmenting a substance in an image acquired by the X-ray machine that has a segmentation criterion as constituent, in the case of which a parameter is calculated in an image area as a measure of a homogeneity of the substance using the method just described.

BRIEF DESCRIPTION OF THE DRAWINGS

Example embodiments of the invention as well as further advantageous refinements of the invention in accordance with the subclaims are illustrated in the following schematics. In the drawings:

DETAILED DESCRIPTION OF THE EXAMPLE EMBODIMENTS

Figure 1:
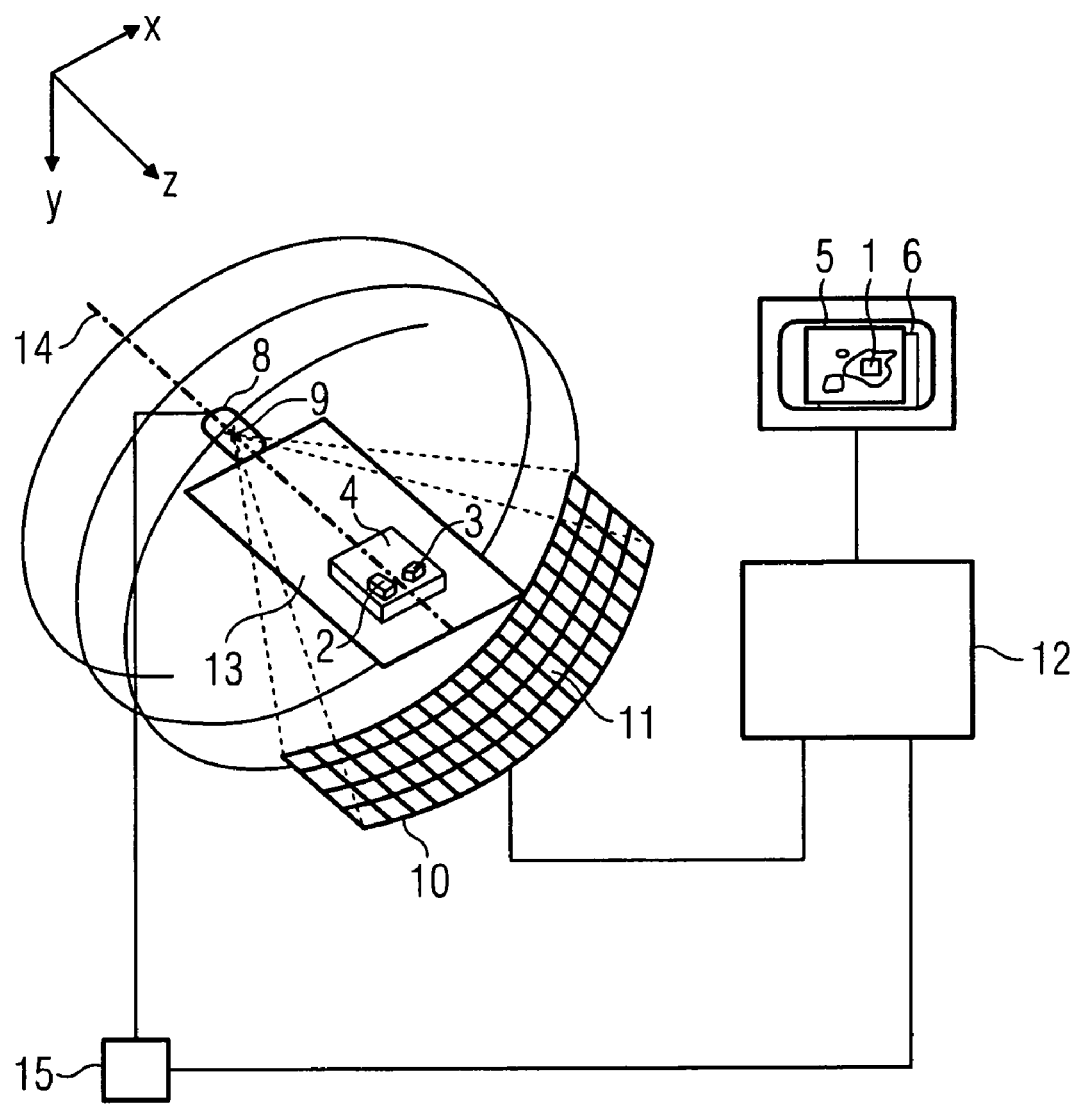
FIG. 1 shows an X-ray machine, partially in a perspective view and partially in a block diagram, with the aid of which the method according to at least one embodiment of the invention for determining a parameter as a measure of a homogeneity of a substance in an image area can be executed.

In order to execute the method according to an embodiment of the invention for determining a parameter H as a measure of the homogeneity of an substance in an image area, it is possible to make use of an X-ray machine known per se—a computed tomography unit, in this example—as it is illustrated in FIG. 1, partially in a perspective view and partially in a block diagram. Such a computed tomography unit has at least one X-ray source—in the form of an X-ray tube 8, here—with at least one focus 9 that generates an X-radiation that strikes a detector 10 situated opposite. The X-ray tube 8 and detector 10 are part of a recording system of the computed tomography unit that is arranged on a rotatable gantry (not illustrated). In the design of the computed tomography unit shown here, the recording system moves in circular fashion about an object 4, for example about a patient, and in so doing scans the object with the aid of the X-radiation.

The absorption of the X-radiation is measured in the detector 10 by a multiplicity of detector elements 11 in the form of attenuation values and transmitted into an arithmetic logic unit 12 where said attenuation values are subsequently stored and processed. A display unit 23 is used to visualize X-ray images. A projection of the object 4 is formed by a set of attenuation values of all the detector elements 11 for a measurement at a specific scanning position of the recording system. It is possible by rotating the recording system to acquire a multiplicity of projections from different projection directions that are required to reconstruct an image in the form of a tomogram or volume image.

By continuously advancing the patient couch 13 along the system axis 14, the object 4 can be scanned not only in a slice, but spirally over a volume that is larger than the extent of the detector 10. A simple variant of the spiral scanning consists in carrying out the advance sequentially such that an advance takes place after each 360° scan, and the actual scanning is undertaken in the state of rest of the object 4. Both variants can be applied in the case of embodiments of the inventive method.

The X-ray voltage of the X-ray tube 8 can be adjusted reciprocally between different voltage values by way of an adjusting apparatus 15 such that different energies of an X-radiation are generated. By way of example, in order to determine a parameter H as a measure of the homogeneity of a substance 2; 3 in an image area 1, projections for at least two different energies E1, E2 of an X-radiation are acquired in relation to each scanning position by a reciprocal adjustment of the X-ray voltage between, for example, 80 kV and 140 kV. Depending on the operating mode of the computed tomography unit, the X-ray voltage can be alternated either at each scanning position or else, for example in the case of a sequential advance, after a complete revolution of the recording system.

As an alternative to the recording system described here, it would also be conceivable to acquire the projections in relation to different energies of an X-radiation by way of an energy-selective detector in the case of a permanently set X-ray voltage. This would have the advantage of being able to dispense with a reciprocal adjustment of the X-radiation.

Reference is further made to the fact that both single-row and multirow detectors can be used. Use can be made of one or more X-ray tubes respectively having one or more foci with, in turn, a single or a number of moving or stationary detectors. The only thing essential to the method is that a beam of fan-shaped design scans the object 4 in a movement of rotation about the system axis 14.

The acquired projections are calculated on the arithmetic logic unit 12 to form two X-ray images 5, 6, the respective X-ray image 5; 6 being reconstructed from the projections only of a specific energy of the X-radiation.

Figure 2:
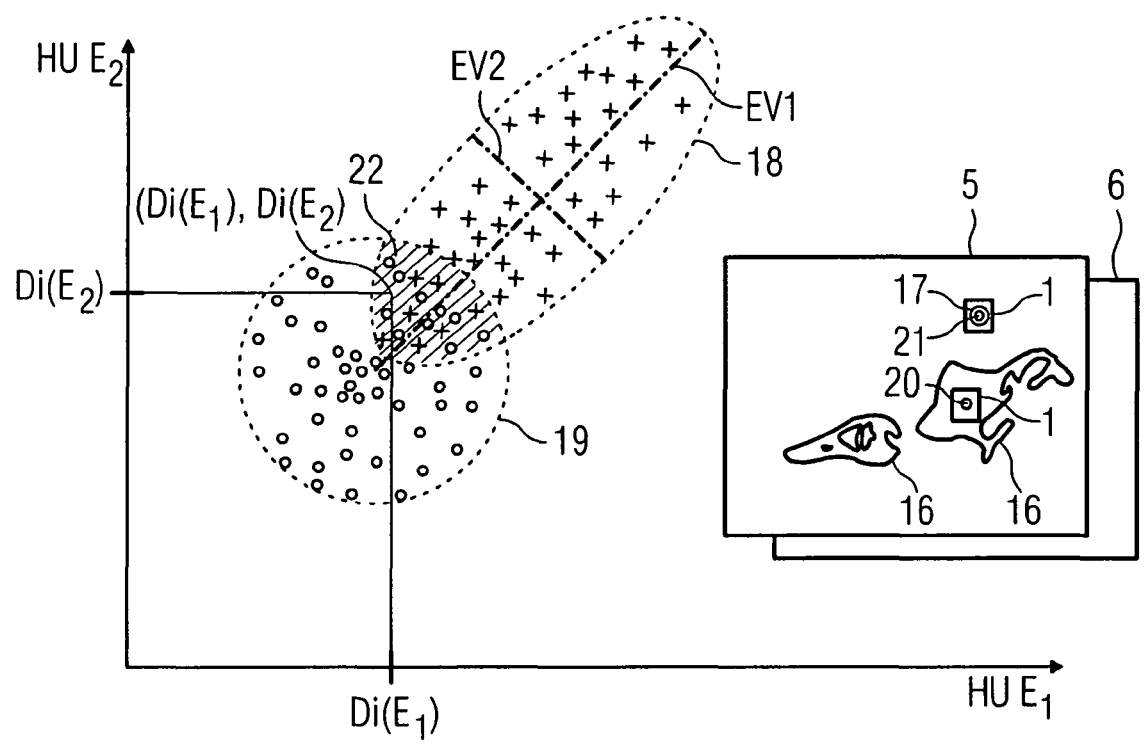
FIG. 2 shows a statistical distribution of pairs of measured values that are respectively formed from two attenuation values of corresponding pixels acquired in relation to different energies.

The attenuation value Di(E1) of the X-ray image 5 reconstructed in relation to the first energy E1 of the X-radiation, and an attenuation value Di(E2) of the X-ray image 6 acquired in relation to the second energy E2 of the X-radiation in this case respectively form for corresponding pixels of the two X-ray images 5, 6 as shown in FIG. 2 a pair of measured values (Di(E1), Di(E2)) of a two-dimensional feature space having the two space axes $HU_{E1}$, $HU_{E2}$. Two different substances 2, 3, specifically bone and iodine, are imaged in the example shown onto two different regions 16, 17 in the two X-ray images 5, 6. The pairs of measured values of the image area 1 are imaged in the feature space at the positions of two different pixels 20, 21, the image area 1 lying at the position of the first pixel 20 in the region 16 of the first substance 2, namely bone, and at the position of the second pixel 21 in the region 17 of the second substance 3, namely iodine.

As illustrated in FIG. 2, the two substances 2, 3 are partly imaged into the same zone 22 of the feature space such that the pixels cannot always be uniquely assigned to a substance 2; 3 on the basis of the individual pair of measured values (Di(E1), Di(E2)). In particular, in this zone 22 of the feature space there is a need for an additional segmentation criterion with the aid of which an improved classification of pixels can be carried out. Such an additional segmentation criterion can be formulated on the basis of the inventive method for determining the parameter H as a measure of the homogeneity of the substance in an image area.

The two substances 2, 3 exhibit different absorption properties with reference to X-radiation as a function of the energy E1; E2. For this reason, the pairs of measured values (Di(E1), Di(E2)) should ideally be imaged onto two different points in the feature space on the assumption of a homogeneous distribution of the substance 2; 3, such that a unique imaging would be ensured at any time.

However, because of anatomical factors in an image region the substances are distributed very differently during examination of a patient, and in reality therefore exhibit substantial differences from one another in homogeneity.

For example, bone is composed of a solid cortical tissue and a trabecular finely structured spongeous tissue, the spongeous tissue being interspersed with blood and/or marrow. Moreover, account is to be taken of variations in the bone composition, variations in the marrow and cavities in the bone. Because of the inhomogeneity of the first substance 2, namely bone, the pairs of measured values of the image area 1 about the first pixel 20, as shown in FIG. 2, are not imaged into a circle 19, but into an ellipse 18 having a preferred direction in feature space.

By contrast thereto, in the image area 1, iodine which is likewise mixed with blood during investigations and is used as contrast medium in order to visualize vessels, is distributed virtually homogeneously about the second pixel 21. Pairs of measured values (Di(E1), Di(E2)) of the second substance 3, namely iodine are imaged in the circle 19 in the feature space, for this reason.

By evaluating the statistical distribution of the pairs of measured values (Di(E1), Di(E2)) in the local image area 1, it is therefore possible to state whether the substance 2; 3 is distributed homogeneously or inhomogeneously. The parameter H as a measure of the homogeneity that is determined from the image area 1 at the position of the respective pixel 20, 21, can be used as additional decision criterion in the segmentation.

Figure 3:
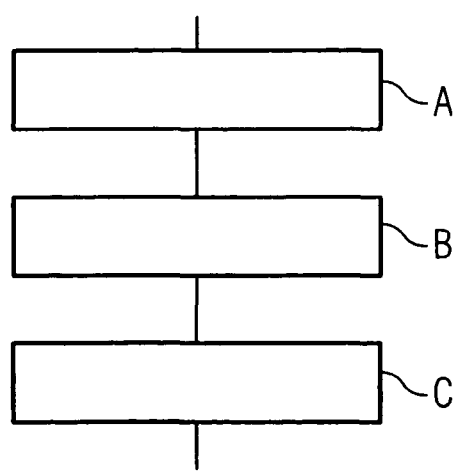
FIG. 3 shows the method according to an embodiment of the invention for calculating the parameter as a measure of the homogeneity of the substance in the image area.

The individual method steps for calculating the parameter H as a measure of the homogeneity of the substance 2; 3 in the image area 1 are illustrated in FIG. 3:

the two X-ray images 5, 6 are acquired for at least two different energies E1, E2 of an X-radiation in a first method step A. The X-ray images 5, 6 respectively include attenuation values Di(E1), Di(E2), where i=1, ..., N, which illustrate an attenuation of the X-radiation passing through the object, N representing the number of pixels present in the image area 1.

Subsequently, pairs of measured values (D1(E1), D1(E2)), ..., (DN(E1), DN(E2)) are formed for corresponding pixels in a second method step B from the attenuation values Di (E1) of the X-ray image 5 acquired in relation to the first energy E1 of the X-radiation, and from the attenuation values Di (E2) of the X-ray image 6 acquired in relation to the second energy E2 of the X-radiation.

The parameter H at the position of the pixel 20 or 21 is calculated in a third method step C as a measure of the homogeneity from the statistical distribution of the pairs of measured values (D1(E1), D1(E2)), ..., (DN(E1), DN(E2)) in image area 1.

In order to determine the statistical distribution, the attenuation values of the pairs of measured values can respectively be written as a vector in a separate fashion for the two different energies:

$$V_{E1}=(D1(E1), D2(E1), \ldots, DN(E1))$$

$$V_{E2}=(D1(E2), D2(E2), \ldots, DN(E2)),$$

$V_{E1}$, and $V_{E2}$ being the two vectors of the attenuation values in relation to different energies E1, E2 of the X-radiation, Di (E1) to Di (E2) being the attenuation value of the ith pixel of the image area 1 acquired at 80 kV and 140 kV, respectively and N being the number of pixels present in the image area 1.

By comparing threshold values, the attenuation values Di(E1), Di(E2) that do not belong to the substance 2; 3, specifically bone or iodine, respectively, of interest here are identified and removed before the calculation. Interfering attenuation values can be removed, for example, by setting their respective value to zero.

The attenuation values Di(E1), Di(E2) are subsequently mean-corrected by calculating a mean D1M and D2M of the attenuation values separately from one another for the energies E1 and E2, and subtracting the calculated mean from the vector components:

$$V'_{E1}=(D1(E1)-D1M, D2(E1)-D1M, \ldots, DN(E1)-D1M)$$

$$V'_{E2}=(D1(E2)-D2M, D2(E2)-D2M, \ldots, DN(E2)-D2M).$$

The two modified vectors $V'_{E1}$ and $V'_{E2}$ subsequently describe the centroid-corrected coordinates of the distribution. The covariance matrix, which reproduces the eccentricity of the distribution, can be specified by analogy with the moment of inertia in classical mechanics:

$$M = \begin{pmatrix} \sum V'^2_{E1} & \sum V'_{E1} \cdot \sum V'_{E2} \\ \sum V'_{E2} \cdot \sum V'_{E1} & \sum V'^2_{E2} \end{pmatrix}$$

M being the covariance matrix formed from the vectors $V'_{E1}$ and $V'_{E2}$.

The two Eigen values EV1, EV2 of the covariance matrix can be determined with the aid of a principle axis transformation carried out using the Jaboci method, for example.

The information relating to the two Eigen values EV1, EV2 of the principle axes is used to obtain the additional segmentation criterion that is required for the improved segmentation of a substance 2; 3 in an X-ray image. Given a homogeneous distribution of the second substance 3, namely iodine in the image area 1, as is the case, for example, for the contrast medium in the form of iodine in a vessel, the two Eigen values EV1, EV2 will differ from one another only slightly. Assuming an uncorrelated measurement noise, the pairs of measured values Di(E1)Di(E2) are distributed in a circle about a point in feature space.

In the case of an inhomogeneous distribution of the first substance 3, namely bone, the two principle axes will differ from one another substantially more plainly.

The following ratio of the two Eigen values EV1, EV2, therefore supplies a scalar parameter H that can be used as a measure of the homogeneity of the substance as an additional decision criterion:

$$H=\text{Min}(EV1, EV2)/\text{Max}(EV1, EV2),$$

EV1 and EV2 being the two Eigen values of the principle axes of the distribution, and H representing the parameter of the homogeneity of the substance in the image area.

The larger the parameter H, the greater is thus the homogeneity of the substance in the image area.

Figure 4:
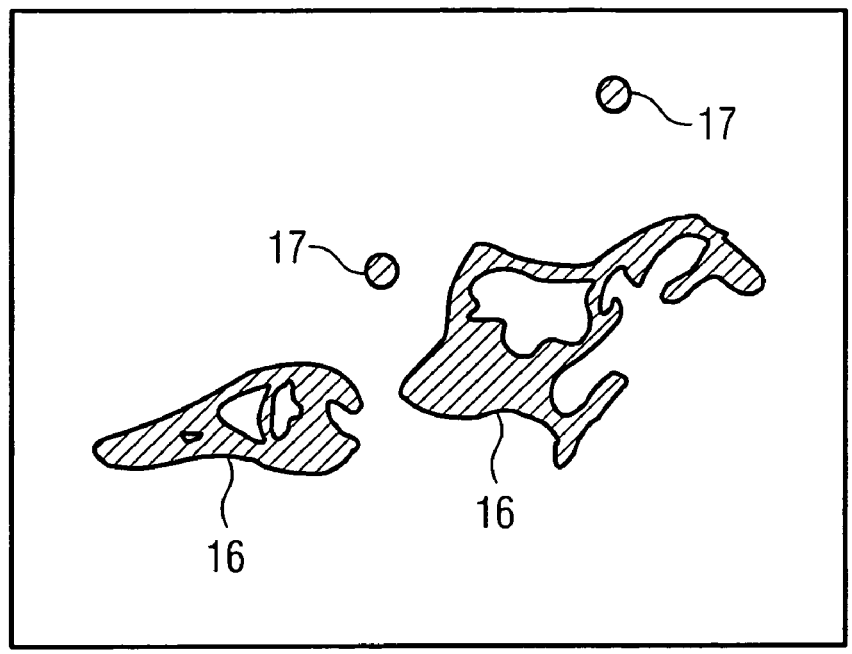
FIG. 4 shows an initial image, calculated from the two X-ray images, of a segmentation of the substance in which bone and vessels are visible.

The improved result of a segmentation of a substance in the case of which the parameter H of homogeneity is used as additional decision criterion may be represented by way of example using the following images:

Illustrated firstly in FIG. 4 is an initial image, calculated from the two X-ray images, of a segmentation that exhibits modified attenuation values. Two different regions 16, 17 are to be seen. The first substance 2, namely bone is imaged in the first region 16, and the second substance 3, namely iodine is imaged in the second region 17. The modified attenuation values are calculated here from a weighted sum of the two attenuation values Di(E1), Di(E2) of respectively corresponding pixels of the two X-ray images 5, 6.

Figure 5:
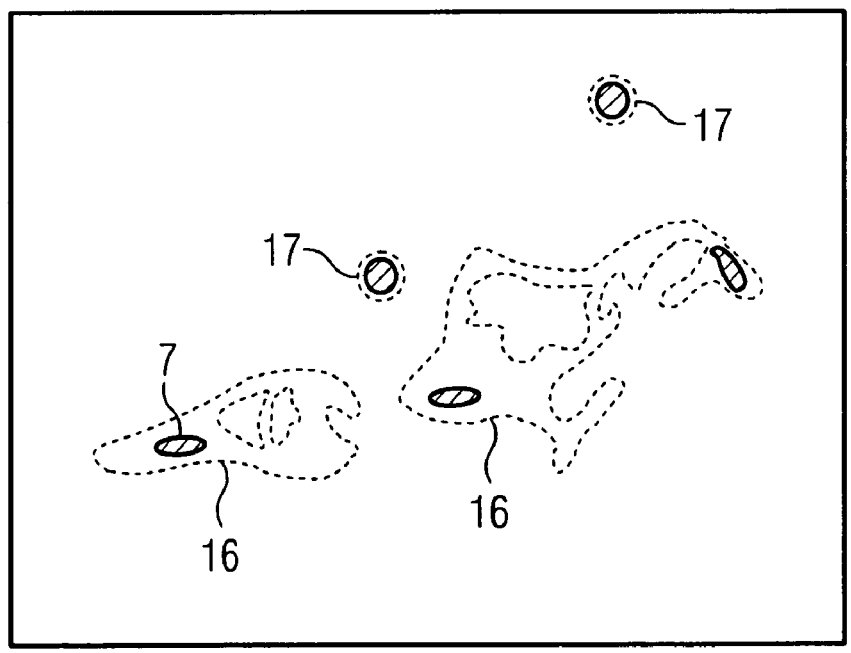
FIG. 5 shows a first result image of a preliminary segmentation in the case of which the segmented pixels are obtained by a first segmentation criterion that takes account of the two attenuation values respectively at the position of an individual pixel.

FIG. 5 shows a first result image of a segmentation of the first substance 2, namely bone, and the second substance 3 namely iodine, the segmentation being obtained by a pixel-referred classification in a two-dimensional feature space, the two dimensions of the feature space respectively being assigned attenuation values Di(E1), Di(E2) of a specific energy E1; E2 of the X-radiation. Faulty classifications 7 occur in the bone, since the attenuation values Di(E1), Di(E2) of a few pixels in the region of the first substance 2, namely bone, exhibit similar values to the second substance 3, namely iodine.

Figure 6:
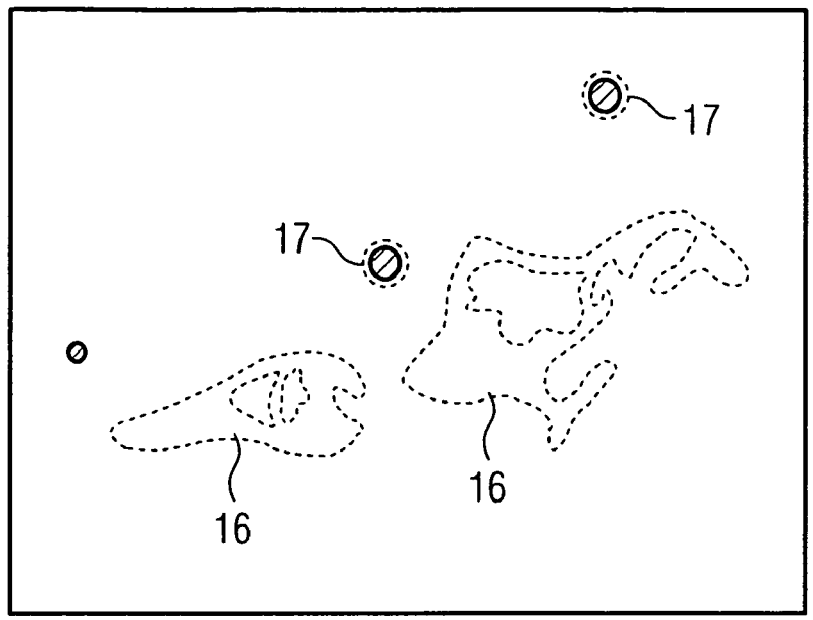
FIG. 6 shows the parameters of all the pixels as a measure of the homogeneity of the substance in the respective image area, in a pictorial illustration.

The result of the calculation of the parameters of the homogeneity are illustrated in FIG. 6 pictorially for all the pixels, the parameters H being calculated from the quotient of the two Eigen values EV1, EV2. In the specific case of this illustration, dark areas stand for high-values of the parameter H, and thus also for a high measure of homogeneity. It is clearly to be seen that a homogeneous distribution is present only in the area of the second substance 3, namely iodine, which is used as contrast medium for examining vessels.

Figure 7:
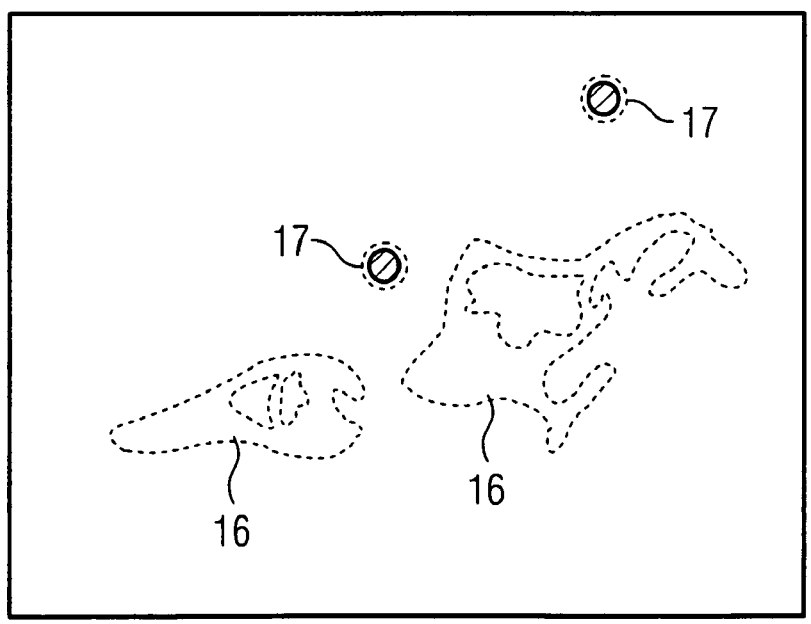
FIG. 7 shows a second result image of an improved segmentation in the case of which the segmented pixels are obtained by an additional second segmentation criterion that takes account of the parameter of the homogeneity in an image area.

FIG. 7 shows a second result image of an improved segmentation in the case of which the parameter H has been used as a measure of the homogeneity in addition to the segmentation criterion used in FIG. 5. Faulty classifications are substantially avoided by virtue of the fact that each pixel classified as the second substance 3, namely iodine, must also exhibit a correspondingly high level of homogeneity.

The idea of at least one embodiment of the invention can be summarized as follows:

at least one embodiment of the invention relates to a method for determining a parameter H in an image area 1 as a measure of homogeneity of a substance 2; 3 in an object 4, and to a method for segmenting a substance 2; 3 in an image that uses the parameter H as additional segmentation criterion in the case of which at least two X-ray images 5, 6 relating to different energies E1, E2 of an X-radiation are acquired, and in the case of which the parameter H is determined from the statistical distribution of attenuation values Di(E1), Di(E2) where i=1, . . . , N in the image region 1 such that faulty classifications 7 can easily be avoided in the segmentation.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for an X-ray machine for determining a parameter in an image area as a measure of a homogeneity of a substance in an object, the method comprising:

acquiring two X-ray images that have attenuation values $Di(E1), Di(E2)$, where $i=1 \ldots N$, that represent an attenuation of the X-radiation passing through the object, for at least two different energies E1, E2 of an X-radiation;

forming, in the image area, measured value pairs $(D1(E1), D1(E2)), \ldots, (DN(E1), DN(E2))$ for corresponding pixels Di from the attenuation values $Di(E1)$ of the X-ray image acquired in relation to the first energy E1 of the X-radiation, and from the attenuation values $Di(E2)$ of the X-ray image acquired in relation to the second energy E2 of the X-radiation; and determining the parameter as a measure of the homogeneity of the substance of the object, respective to an area surrounding the object, by evaluating a statistical distribution of the measured value pairs $(D1(E1), D1(E2)), \ldots, (DN(E1), DN(E2))$ of the image area.

2. The method as claimed in claim 1, wherein the evaluation of the statistical distribution comprises a principle axis transformation for calculating two Eigen values EV1, EV2 of the principle axes of the distribution.

3. The method as claimed in claim 2, wherein the parameter is calculated from a quotient of the two Eigen values EV1, EV2, and the quotient is formed with the smaller of the two Eigen values EV1, EV2 in the numerator and the larger in the denominator.

4. The method as claimed in claim 1, wherein the image area extends at least over 5 pixels in each image dimension.

5. The method as claimed in claim 1, wherein the acquired X-ray images are tomograms of the object.

6. The method as claimed in claim 1, wherein the acquired X-ray images are volume images of the object.

7. The method as claimed in claim 1, wherein the first energy E1 of the X-radiation is generated with the X-ray voltage set at 80 kV, and the second energy E2 with the X-ray voltage set at 140 kV.

8. The method as claimed in claim 1, wherein those attenuation values of the pixels that do not belong to the substance are identified and removed before the step of forming.

9. The method as claimed in claim 8, wherein the identification is performed by calculating the attenuation values of corresponding pixels with one another and comparing them with a threshold value.

10. The method as claimed in claim 1, wherein bone is the substance for which the parameter is calculated.

11. The method as claimed in claim 1, wherein iodine is the substance for which the parameter is calculated.

12. A method for an X-ray machine for segmenting a substance in an image acquired by the X-ray machine that has a segmentation criterion as constituent, wherein the parameter in a respective image area is determined as a measure of a homogeneity of the substance in accordance with the method of claim 1.

13. The method as claimed in claim 2, wherein the image area extends at least over 5 pixels in each image dimension.

14. The method as claimed in claim 2, wherein the acquired X-ray images are tomograms of the object.

15. The method as claimed in claim 2, wherein the acquired X-ray images are volume images of the object.

16. The method as claimed in claim 2, wherein bone is the substance for which the parameter is calculated.

17. The method as claimed in claim 2, wherein iodine is the substance for which the parameter is calculated.

18. A computer readable medium including program segments for, when executed on a computer, causing the computer to implement the method of claim 1.

19. A method for an X-ray machine for determining a parameter in an image area as a measure of a homogeneity of a substance in an object, the method comprising:

acquiring two X-ray images that have attenuation values $Di(E1), Di(E2)$, where $i=1 \ldots N$, that represent an attenuation of the X-radiation passing through the object, for at least two different energies E1, E2 of an X-radiation;

respectively normalizing the attenuation values $Di(E1), Di(E2)$ of the two X-ray images in the image area by subtracting from the respective attenuation value a mean attenuation value DM1; DM2 calculated in the image area of the respective X-ray image;

forming, in the image area, measured value pairs $(D1(E1), D1(E2)), \ldots, (DN(E1), DN(E2))$ for corresponding pixels Di from the attenuation values $Di(E1)$ of the X-ray image acquired in relation to the first energy E1 of the X-radiation, and from the attenuation-values $Di(E2)$ of the X-ray image acquired in relation to the second energy E2 of the X-radiation; and determining the parameter as a measure of the homogeneity of the substance of the object, respective to an area surrounding the object, by evaluating a statistical distribution of the measured value pairs $(D1(E1), D1(E2)), (DN(E1), DN(E2))$ of the image area.

* * * * *